(12) United States Patent
Radicone

(10) Patent No.: US 10,646,608 B2
(45) Date of Patent: May 12, 2020

(54) SYSTEM AND METHOD FOR DISINFECTING A SURFACE OF AN OBJECT WITH IODINE-LADEN GAS

(71) Applicant: i 2 Air Fluid Innovation, Inc., Huntington Station, NY (US)

(72) Inventor: Michael C. Radicone, Huntington Station, NY (US)

(73) Assignee: i 2 Air Fluid Innovation, Inc., Huntington Station, NY (US)

(*) Notice: Subject to any disclaimer, the term of this patent is extended or adjusted under 35 U.S.C. 154(b) by 0 days.

(21) Appl. No.: 16/595,731

(22) Filed: Oct. 8, 2019

(65) Prior Publication Data

US 2020/0030475 A1    Jan. 30, 2020

Related U.S. Application Data

(62) Division of application No. 15/689,709, filed on Aug. 29, 2017, now Pat. No. 10,471,166.

(60) Provisional application No. 62/447,152, filed on Jan. 17, 2017.

(51) Int. Cl.
  *A61L 2/20* (2006.01)
  *C01B 7/14* (2006.01)
(52) U.S. Cl.
  CPC ............... *A61L 2/20* (2013.01); *C01B 7/14* (2013.01); *A61L 2202/11* (2013.01)

(58) Field of Classification Search
  CPC .......... A61L 2/16; A61L 2/20; A61L 2202/10; A61L 2202/11; C01B 7/14
  See application file for complete search history.

(56) References Cited

U.S. PATENT DOCUMENTS

| 7,067,089 B2* | 6/2006 | Wen ........................ A23L 3/28 422/28 |
| 8,696,997 B2* | 4/2014 | Hancock .................. A61L 2/14 118/723 MW |
| 2004/0022673 A1* | 2/2004 | Protic ...................... A61L 2/20 422/28 |

* cited by examiner

*Primary Examiner* — Timothy C Cleveland
(74) *Attorney, Agent, or Firm* — Stites & Harbison, PLLC; David W. Nagle, Jr.

(57) ABSTRACT

In a system and method for disinfecting a surface of an object with iodine-laden gas, a carrier gas generation means generates a gas stream, which is then directed into a chamber that includes an iodine source. As the gas stream enters and passes through the chamber, iodine is drawn and absorbed into the gas stream, creating an iodine-laden gas that exits the chamber. In some embodiments, the iodine-laden gas then travels from the chamber and is directed into an enclosure when it interacts with microbes contained on a surface of an object housed within the enclosure or otherwise engaged by the enclosure. In other embodiments, as the iodine-laden gas exits the chamber, it is directed to a nozzle, via which the iodine-laden gas is applied to the surface of the object to be disinfected.

12 Claims, 4 Drawing Sheets

SYSTEM AND METHOD FOR DISINFECTING A SURFACE OF AN OBJECT WITH IODINE-LADEN GAS

CROSS-REFERENCE TO RELATED APPLICATIONS

Figure 1:
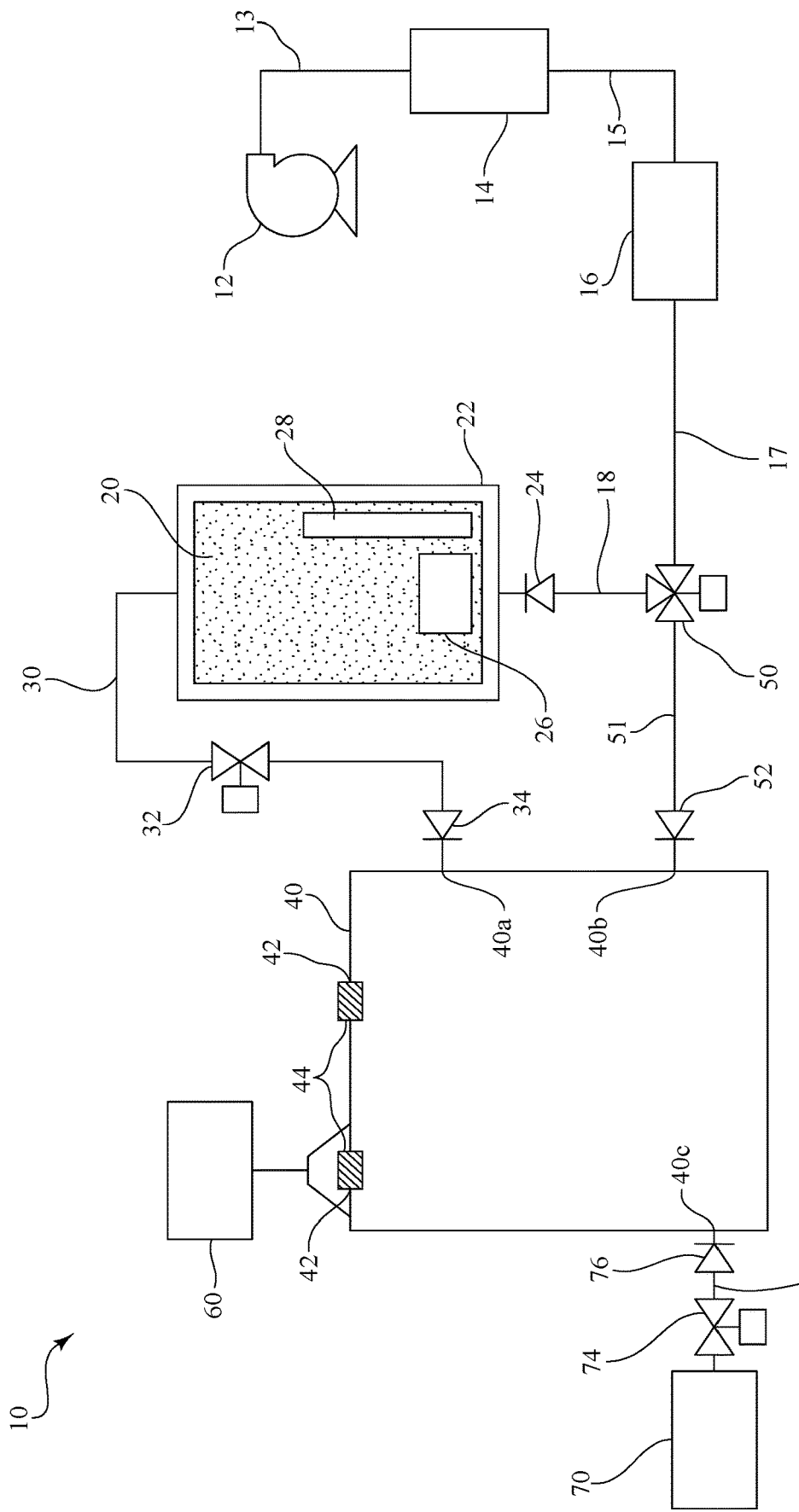

The present application is a divisional of U.S. patent application Ser. No. 15/689,709 filed on Aug. 29, 2017, which claims priority to U.S. Patent Application Ser. No. 62/447,152 filed on Jan. 17, 2017, the entire disclosure of which is incorporated herein by reference.

BACKGROUND OF THE INVENTION

Iodine has long been used for disinfection. Iodine is a member of the halogen group, which includes bromine, fluorine and chlorine, all known antimicrobials. Among the various iodine species, both elemental iodine ($I_2$) and hypoiodous acid have disinfection capability, whereas iodide and iodates do not. The antimicrobial action of elemental iodine is, like all halogens, as an extremely potent oxidizer. Elemental iodine reacts in electrophilic reactions with enzymes of the respiratory chain, as well as with amino acids located in cell membrane and cell wall proteins. The well-balanced tertiary structure necessary for maintaining the respiratory chain and cell integrity is destroyed, and the microorganism is irreversibly damaged. It is speculated that iodine molecules penetrate the cell wall of microorganisms and inflict structural damage on the capsid protein. Halogen disinfection is a form of chemical sterilization in which oxidation of cell constituents and halogenations of cell proteins occurs. At the same time, based on a review of the available toxicology data, in July 2006, the United States Environmental Protection Agency (EPA) concluded that iodine and iodophor complexes are of very low toxicity by the oral, dermal, and inhalation routes of exposure. In short, elemental iodine and its complexes are simple and inexpensive antimicrobials that are useful as disinfecting agents.

Iodine, like other oxidizing biocides, may be rendered ineffectual when reduced or oxidized through organic contact in solutions. Therefore, being able to expose microbes on surfaces to elemental iodine without organic or fluid interference may offer the means to provide significant disinfection. It is therefore an object of the present invention to generate a significant quantity of elemental iodine-laden gas (or vapor), a known disinfectant, for presentation so as to have an antimicrobial action on the surface of an object.

SUMMARY OF THE INVENTION

The present invention is a system and method for disinfecting a surface of an object with iodine-laden gas.

An exemplary system made in accordance with the present invention includes a carrier gas generation means (preferably in the form of a compressor, blower, or pressurized tank), which generates a gas stream. This gas stream may be simply an air stream, or it could be comprised of other carrier gases, such as carbon dioxide ($CO_2$), oxygen ($O_2$), nitrogen ($N_2$), argon (AR), other inert gases, and combinations thereof. In some embodiments, the gas stream travels from the gas generation means to and through a heater to raise the temperature of the gas stream. In some embodiments, the gas stream also passes through a negative ion generator that uses high voltage to ionize (or electrically charge) the air molecules.

Whether or not the gas stream is heated and/or electrically charged, it is directed into a chamber that includes an iodine source. As the gas stream enters and passes through the chamber, iodine is drawn into and absorbed into the gas stream. Furthermore, during downtime, the chamber, with the iodine source, acts as a reservoir, extending the exposure to the iodine source and facilitating the introduction of iodine into the air held within the chamber.

The iodine-laden gas then travels from the chamber and is directed into an enclosure. While within the enclosure, the iodine-laden gas interacts with microbes contained on the surfaces of objects housed within the enclosure.

In some embodiments, the enclosure is substantially sealed to prevent the escape of iodine vapor into the surrounding atmosphere. Thus, the enclosure may be provided with a door, so that it can be selectively opened to receive objects, and then closed prior to the introduction of the iodine-laden gas into the enclosure. In such embodiments, the enclosure is provided with vents, as there must be some means for air to escape the enclosure as it fills with iodine-laden gas. Such vents are provided with carbon filters that capture and prevent escape of the iodine into the surrounding atmosphere. Furthermore, objects may be strategically placed in the enclosure in the vicinity of the vents to ensure flow of the iodine-laden gas over and around the surfaces of the objects.

As a further refinement, the system may be provided with a means to flush the iodine-laden gas from the enclosure. As a further refinement, the system may be provided with a vacuum source (or suction) that pulls iodine-laden gas through the enclosure via one of the vents; thus, the iodine-laden gas may be simultaneously introduced (pushed) into the enclosure while it is withdrawn (pulled) through a vent under vacuum pressure. As yet a further refinement, the enclosure may be in fluid communication with a source of cleaning solution, such that the cleaning solution (e.g., water or water mixed with a detergent and/or a biocide) can be selectively introduced into the enclosure at any time to rinse objects within the enclosure and/or the interior of the enclosure itself.

With respect to the system described above, a method for disinfecting a surface of an object thus generally comprises the steps of: (i) providing a chamber including an iodine source; (ii) generating a carrier gas stream for introduction into and through the chamber including the iodine source, such that an iodine-laden gas exits the chamber; (iii) providing an enclosure and housing the object within the enclosure; and (iv) introducing the iodine-laden gas into the enclosure.

Rather than using a substantially sealed enclosure to house the object, in some embodiments, the enclosure has an open side, which is placed over and/or engages the object to be disinfected. In such a system, a method for disinfecting a surface of an object thus generally comprises the steps of: (i) providing a chamber including an iodine source; (ii) generating a carrier gas stream for introduction into and through the chamber including the iodine source, such that an iodine-laden gas exits the chamber; (iii) providing an enclosure having an open side, and placing the enclosure over or on the surface of the object; and (iv) introducing the iodine-laden gas into the enclosure, where it interacts with microbes contained on the surface of the object.

Rather than using an enclosure to house or engage the object, in some embodiments, as the iodine-laden gas exits the chamber, it is directed to a nozzle. The iodine-laden gas is then ejected from the nozzle and applied to the surface of the object to be disinfected. In such a system, a method for disinfecting a surface of an object thus generally comprises the steps of: (i) providing a chamber including an iodine source; (ii) generating a carrier gas stream for introduction into and through the chamber including the iodine source, such that an iodine-laden gas exits the chamber and into a conduit for delivery to a nozzle; and (iii) ejecting the iodine-laden gas via the nozzle onto the surface of the object, where it interacts with microbes contained on the surface of the object.

DESCRIPTION OF THE DRAWINGS

FIG. 1 is a schematic view of an exemplary system made in accordance with the present invention;

FIG. 2 is a block diagram that illustrates a control logic for the exemplary system of FIG. 1;

FIG. 3 is a schematic view of another exemplary system made in accordance with the present invention; and FIG. 4 is a schematic view of another exemplary system made in accordance with the present invention.

DETAILED DESCRIPTION OF THE INVENTION

The present invention is a system and method for disinfecting a surface of an object with iodine-laden gas.

FIG. 1 is a schematic view of an exemplary system 10 made in accordance with the present invention. As shown, the system 10 includes a carrier gas generation means 12 (preferably in the form of a compressor, blower, or pressurized tank), which generates a gas stream. This gas stream may be simply an air stream, or it could be comprised of other carrier gases, such as carbon dioxide ($CO_2$), oxygen ($O_2$), nitrogen ($N_2$), argon (AR), other inert gases, and combinations thereof. In this exemplary embodiment, the gas stream travels from the gas generation means 12 through a conduit 13, which directs the gas stream to and through a heater 14 to raise the temperature of the gas stream, the importance of which is further described below. In this exemplary embodiment, and as also shown in FIG. 1, the gas stream then travels from the heater 14 through a conduit 15, which directs the gas stream to a negative ion generator 16 that uses high voltage to ionize (or electrically charge) the air molecules, the importance of which is further described below.

Referring still to FIG. 1, the gas stream exits the negative ion generator 16 and is then directed into and passes through an iodine source 20. In this exemplary embodiment, the gas stream travels through a conduit 17 to a three-way (or diverter) valve 50, the use and function of which is described below. From the three-way valve 50, all or a portion of the gas stream travels through a conduit 18 through a check valve 24 and into a chamber 22 that includes the iodine source 20. As the gas stream enters and passes through the chamber 22, iodine is drawn and absorbed into the gas stream. Furthermore, during downtime, the chamber 22, with the iodine source 20, acts as a reservoir, extending the exposure to the iodine source 20 and facilitating the introduction of iodine into the air held within the chamber 22.

The iodine source 20 may be iodinated resin or iodine crystals or particles of varying size. Various commercially available iodine resins (preferably non-allergenic resins) in crushed or small bead form (i.e., beads coated with iodine), or blends thereof, may be used in the chamber 22. For instance, the chamber 22 may be a substantially hollow and open-ended column packed with crushed and/or beaded iodine resin, as greater surface area leads to enhanced transfer of iodine to the gas stream. For example, an iodine resin distributed by The Purolite Company of Bala Cynwyd, Pa. under Model No. 605 may be used in the chamber 22. Of course, the chamber 22 is constructed of materials (such as stainless steel or plastic) that are not adversely affected by the iodine source 20 or vapor, and the chamber 22 is preferably replaceable based on iodine depletion and needs.

Furthermore, as shown in FIG. 1, in some embodiments, the chamber 22 includes a static mixer 26 to agitate the iodine source 20, causing it to percolate and rise, rotating and exposing different surfaces of the particles of iodine to the gas stream.

As mentioned above, in this exemplary embodiment, the gas stream is first passed through a heater 14 before it encounters the iodine source 20. The elevated air temperature (for example, approximately 100° F.) also leads to greater transfer of iodine to the gas stream. Additionally, or alternatively, the chamber 22 may be provided with a heater 28 to achieve the same end. Whether or not such heating of the gas stream and/or iodine source 20 is necessary or desired is dependent on the environment in which the system is operating and the desired level of iodine output.

As also mentioned above, in this exemplary embodiment, the gas stream is also passed through a negative ion generator 16 before it encounters the iodine source 20. The negative ion generator 16 uses high voltage to ionize (or electrically charge) the air molecules, which cause positively charged iodine molecules to be attracted into the gas stream. Whether or not such charging of the gas stream is necessary or desired is dependent on the environment in which the system is operating and the desired level of iodine output.

The iodine-laden gas is then directed via a conduit 30, such as a fluoridated plastic or stainless-steel tube, into an enclosure 40 via an inlet opening 40*a*. In this exemplary embodiment, flow of the iodine-laden gas through the conduit 30 is controlled by a valve 32 (such as a solenoid valve). When the valve 32 is open, the iodine-laden gas passes through a check valve 34 before entering the enclosure 40 via the inlet opening 40*a*. While within the enclosure 40, the iodine-laden gas interacts with microbes contained on the surfaces of objects housed within the enclosure 40. In this regard, the enclosure 40 is substantially sealed to prevent the escape of iodine vapor into the surrounding atmosphere. Thus, the enclosure 40 may be provided with a door (not shown), so that it can be selectively opened to receive objects, and then closed prior to the introduction of the iodine-laden gas into the enclosure 40. However, as shown in FIG. 1, the enclosure 40 is provided with vents 42, as there must be some means for air to escape the enclosure 40 as it fills with iodine-laden gas. Such vents 42 are provided with carbon filters 44 that capture and prevent escape of the iodine into the surrounding atmosphere. Furthermore, objects may be strategically placed in the enclosure 40 in the vicinity of the vents 42 to ensure flow of the iodine-laden gas over and around the surfaces of the objects.

As also shown in FIG. 1, the system 10 may be provided with a means to flush the iodine-laden gas from the enclosure 40. In this exemplary embodiment, as mentioned above, there is a three-way valve 50 that allows a portion of the gas stream to be diverted before it enters into the chamber 22, such that air without iodine can be directed into the enclosure 40 via a conduit 51 and through an inlet opening 40*b*. In this exemplary embodiment, the air passes through a check valve 52 before entering the enclosure 40 via the inlet opening 40b. As such air enters the enclosure 40, it forces any remaining iodine-laden gas through the carbon filters 44.

As a further refinement, and as also shown in FIG. 1, the system 10 may be provided with a vacuum source 60 (or suction) that pulls iodine-laden gas through the enclosure 40 via one of the vents 42. In other words, the iodine-laden gas may be simultaneously introduced (pushed) into the enclosure 40 via the inlet opening 40b while it is withdrawn (pulled) through a vent 42 under vacuum pressure.

As a further refinement, and as also shown in FIG. 1, the enclosure 40 of the system 10 may be in fluid communication with a source of cleaning solution 70, such that the cleaning solution (e.g., water or water mixed with a detergent and/or a biocide) can be selectively introduced into the enclosure 40 via a conduit 72 and an inlet opening 40c. In this exemplary embodiment, flow of the cleaning solution through the conduit 72 is controlled by a valve 74 (such as a solenoid valve). When the valve 74 is open, the cleaning solution passes through a check valve 76 before entering the enclosure 40 via the inlet opening 40c. The cleaning solution could be used to rinse objects within the enclosure 40 and/or the interior of the enclosure 40 itself. Alternatively, the cleaning solution could be introduced into the enclosure 40 before the iodine-laden gas to remove contaminants prior to disinfection.

As a further refinement, although not shown in FIG. 1, the system 10 may be provided with a means (such as a negative ion generator) by which to apply a negative electrostatic charge to objects within the enclosure 40 prior to the introduction of the iodine-laden gas.

Examples of objects that can be placed into the enclosure for disinfection include, but are not limited to: bottles or other storage receptacles; clothing or similar fabrics; agricultural products, such as fruits and nuts; milking devices or equipment from dairy farming operations; and medical devices, such as colonoscopy wands.

Figure 2:
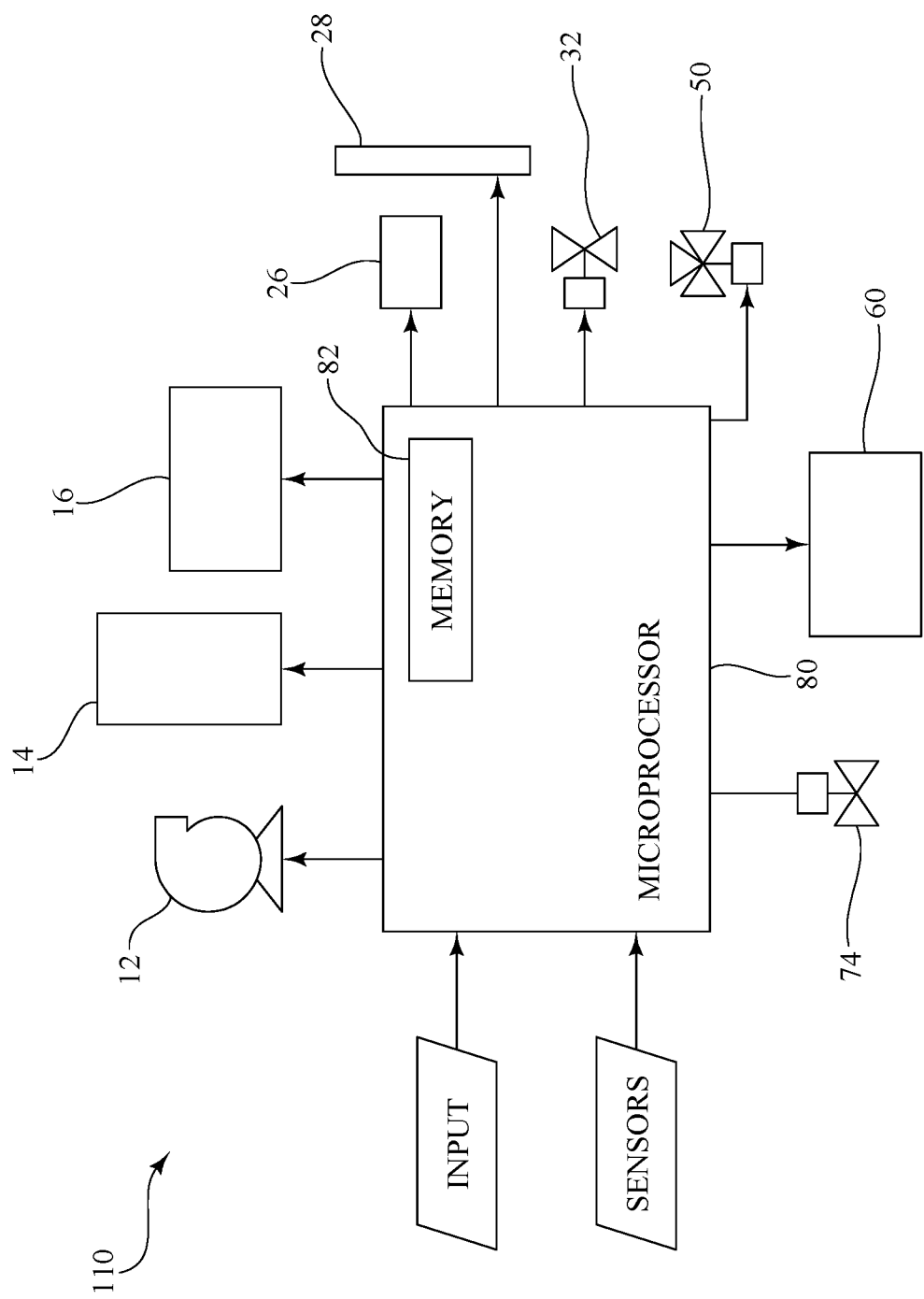

FIG. 2 is a block diagram that illustrates a control logic for the exemplary system 10 of FIG. 1. As shown, such a control logic includes a microprocessor 80 with a memory component 82. The gas generation means 12 is operably connected to and receives control signals from the microprocessor 80, i.e., an on/off signal. If present, the heater 14 and negative ion generator 16 are operably connected to and receive control signals from the microprocessor 80. Similarly, if present, the static mixer 26 and the heater 28 in the chamber 22 are operably connected to and receive control signals from the microprocessor 80. Each of the valves 32, 50, and 74 is operably connected to and receives control signals from the microprocessor 80. Finally, the vacuum source 60 (or suction) is operably connected to and receives control signals from the microprocessor 80. Accordingly, each of these components could be operated in response to user input. For instance, certain controls could be provided on a panel secured to the enclosure 40 to allow for such user input. Furthermore, preprogrammed routines could be stored in the memory component 82 to automate the process. For example, the user may simply have to press a button to activate a preprogrammed routine.

Referring still to FIG. 2, it is also contemplated that one or more sensors could be operably connected to the microprocessor 80 to monitor the operation of the system. For example, sensors could be provided within the enclosure 40 to monitor iodine levels or pressure within the enclosure 40.

Finally, with respect to the exemplary system illustrated in FIGS. 1 and 2, a method for disinfecting a surface of an object thus comprises the steps of: (i) providing a chamber 22 including an iodine source 20; (ii) generating a carrier gas stream for introduction into and through the chamber 22 including the iodine source 20, such that an iodine-laden gas exits the chamber 22; (iii) providing an enclosure 40 and housing the object within the enclosure 40; and (iv) introducing the iodine-laden gas into the enclosure 40. Additionally, in some implementations, and as described above, the method may include intermediate steps of heating the iodine-laden gas and/or electrically charging the iodine-laden gas. After the iodine-laden gas has been introduced into the enclosure 40, in some implementations, and as also described above, the method may include the steps of applying a vacuum 60 to the enclosure and/or rinsing the object within the enclosure with a cleaning solution.

Figure 3:
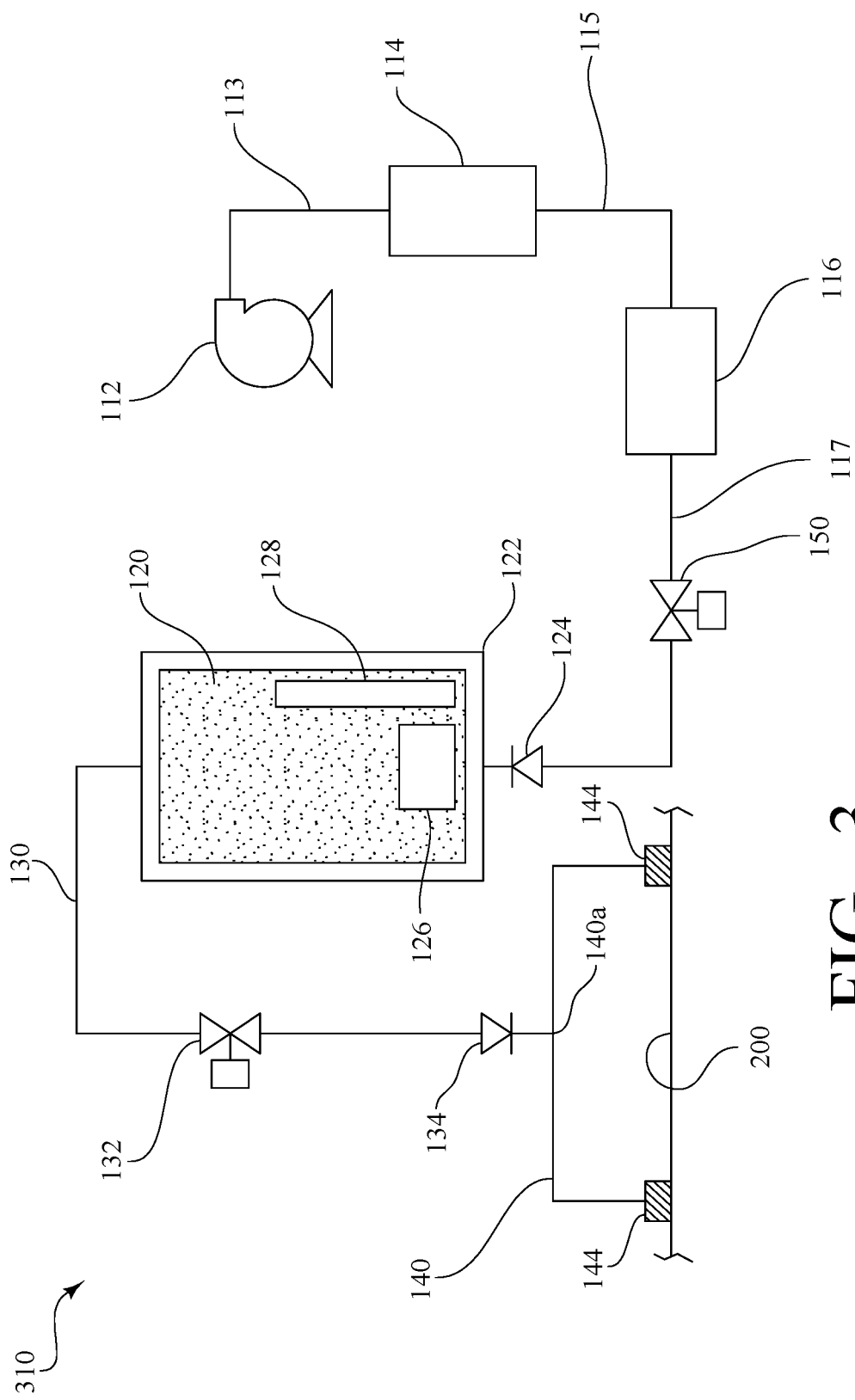

FIG. 3 is a schematic view of another exemplary system 110 made in accordance with the present invention. As shown, the system 110 is very similar to that described above with reference to FIG. 1, except that the enclosure 140 has an open side, which is placed over and/or engages the object to be disinfected, as further described below.

As shown in FIG. 3, the system 110 includes a carrier gas generation means 112 (preferably in the form of a compressor, blower, or pressurized tank), which generates a gas stream. Again, this gas stream may be simply an air stream, or it could be comprised of other carrier gases, such as carbon dioxide ($CO_2$), oxygen ($O_2$), nitrogen ($N_2$), argon (AR), other inert gases, and combinations thereof. In this exemplary embodiment, the gas stream travels from the gas generation means 112 through a conduit 113, which directs the gas stream to and through a heater 114 to raise the temperature of the gas stream. In this exemplary embodiment, the gas stream then travels from the heater 114 through a conduit 115, which directs the gas stream to a negative ion generator 116 that uses high voltage to ionize (or electrically charge) the air molecules.

Referring still to FIG. 3, the gas stream exits the negative ion generator 116 and is then directed into and passes through an iodine source 120. In this exemplary embodiment, the gas stream travels through a conduit 117 to a valve 150 (such as a solenoid valve), which controls flow of the gas stream to the iodine source 120. When the valve 150 is open, the gas stream passes through a check valve 124 and into a chamber 122 that includes the iodine source 120. As with the chamber 22 described above with reference to FIG. 1, as the gas stream enters and passes through the chamber 122, iodine is drawn and absorbed into the gas stream. Furthermore, as also described above with reference to FIG. 1, in some embodiments, the chamber 122 includes a static mixer 126 to agitate the iodine source 120, causing it to percolate and rise, rotating and exposing different surfaces of the particles of iodine to the gas stream. The chamber 122 may also be provided with a heater 128 to achieve the same end.

Referring still to FIG. 3, the iodine-laden gas is then directed via a conduit 130, such as a fluoridated plastic or stainless-steel tube, into an enclosure 140 via an inlet opening 140a. In this exemplary embodiment, flow of the iodine-laden gas through the conduit 130 is controlled by a valve 132 (such as a solenoid valve). When the valve 132 is open, the iodine-laden gas passes through a check valve 134 before entering the enclosure 140 via the inlet opening 140a. In this exemplary embodiment, however, the enclosure 140 has an open side, which is placed over and/or engages a surface 200 of the object to be disinfected.

Referring still to FIG. 3, in this exemplary embodiment, carbon filters 144 are installed around the rim or periphery of the open side of the enclosure 140. Thus, when the open side of the enclosure 140 is placed against the surface 200 of the object to be disinfected, the carbon filters 144 not only capture and prevent escape of the iodine into the surrounding atmosphere, but also function as a seal against the surface (i.e., the surface of the object itself or a floor or underlying surface below the object).

As a further refinement, although not shown in FIG. 3, the enclosure 140 of the system 110 may be in fluid communication with a source of cleaning solution, such that the cleaning solution (e.g., water or water mixed with a detergent and/or a biocide) can be selectively introduced into the enclosure 140 to rinse objects within the enclosure 140 and/or the interior of the enclosure 140 itself.

Examples of objects that can be disinfected in this manner include, but are not limited to: floor surfaces; wall surfaces; body tissue, such a wound; or portal area, such as a catheter port.

Finally, with respect to the exemplary system illustrated in FIG. 3, a method for disinfecting a surface of an object thus comprises the steps of: (i) providing a chamber 122 including an iodine source 120; (ii) generating a carrier gas stream for introduction into and through the chamber 122 including the iodine source 120, such that an iodine-laden gas exits the chamber 122; (iii) providing an enclosure 140 having an open side, and placing the enclosure 140 over or on the surface of the object; and (iv) introducing the iodine-laden gas into the enclosure 140, where it interacts with microbes contained on the surface of the object. Additionally, in some implementations, and as described above, the method may include intermediate steps of heating the iodine-laden gas and/or electrically charging the iodine-laden gas.

Figure 4:
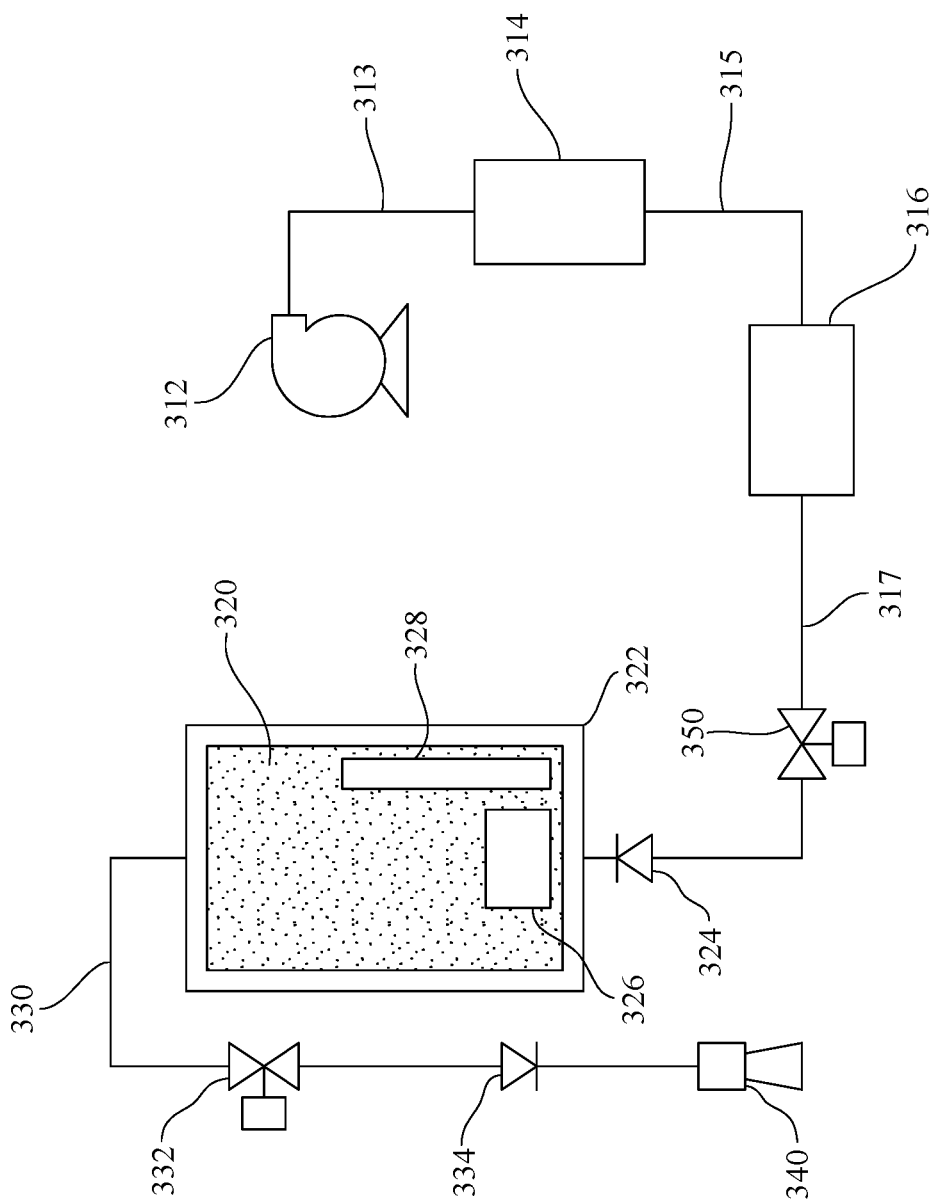

FIG. 4 is a schematic view of another exemplary system 310 made in accordance with the present invention. As shown, the system 310 is very similar to that described above with reference to FIG. 3. Specifically, as shown in FIG. 4, the system 310 includes a carrier gas generation means 312 (preferably in the form of a compressor, blower, or pressurized tank), which generates a gas stream. Again, this gas stream may be simply an air stream, or it could be comprised of other carrier gases, such as carbon dioxide ($CO_2$), oxygen ($O_2$), nitrogen ($N_2$), argon (AR), other inert gases, and combinations thereof. In this exemplary embodiment, the gas stream travels from the gas generation means 312 through a conduit 313, which directs the gas stream to and through a heater 314 to raise the temperature of the gas stream. In this exemplary embodiment, the gas stream then travels from the heater 314 through a conduit 315, which directs the gas stream to a negative ion generator 316 that uses high voltage to ionize (or electrically charge) the air molecules.

Referring still to FIG. 4, the gas stream exits the negative ion generator 316 and is then directed into and passes through an iodine source 320. In this exemplary embodiment, the gas stream travels through a conduit 317 to a valve 350 (such as a solenoid valve), which controls flow of the gas stream to the iodine source 320. When the valve 350 is open, the gas stream passes through a check valve 324 and into a chamber 322 that includes the iodine source 320. As with the chamber 22 described above with reference to FIG. 1 and the chamber 122 described above with reference to FIG. 3, as the gas stream enters and passes through the chamber 322, iodine is drawn and absorbed into the gas stream. Furthermore, as also described above with reference to FIGS. 1 and 3, in some embodiments, the chamber 322 includes a static mixer 326 to agitate the iodine source 320, causing it to percolate and rise, rotating and exposing different surfaces of the particles of iodine to the gas stream. The chamber 322 may also be provided with a heater 328 to achieve the same end.

Referring still to FIG. 4, the iodine-laden gas is then directed via a conduit 330, such as a fluoridated plastic or stainless-steel tube, to a nozzle 340. In this exemplary embodiment, flow of the iodine-laden gas through the conduit 330 is controlled by a valve 332 (such as a solenoid valve). When the valve 332 is open, the iodine-laden gas passes through a check valve 334 before entering the nozzle 340. The iodine-laden gas is thus ejected from the nozzle 340 and applied to the surface of the object to be disinfected.

As a further refinement, although not shown in FIG. 4, the nozzle 340 may also be in fluid communication with a source of cleaning solution, such that the cleaning solution (e.g., water or water mixed with a detergent and/or a biocide) can also be selectively ejected through the nozzle 340. The cleaning solution could be used to rinse objects after disinfection. Alternatively, the cleaning solution could be applied before the iodine-laden gas to remove contaminants prior to disinfection.

Examples of objects that can be disinfected in this manner include, but are not limited to: conduits, such as a milk conduit in a dairy farming operation; and enclosures, such as a milking inflation in a dairy farming operation.

With respect to the use of the exemplary system 310 illustrated in FIG. 4 for cleaning a conduit or similar fluid transport device, the iodine-laden gas may be introduced into the conduit at one end, while another end (or ends) is closed, such that the iodine-laden gas flow is under pressure with the conduit to ensure interaction with the interior surfaces of the conduit for disinfection. Furthermore, when iodine-laden gas is released or forced from the conduit, it may be passed through a carbon filter that captures and prevents escape of the iodine into the surrounding atmosphere. For example, heat exchangers, ballast tanks, and storage containers can be disinfected in this manner.

Finally, with respect to the exemplary system illustrated in FIG. 4, a method for disinfecting a surface of an object thus comprises the steps of: (i) providing a chamber 322 including an iodine source 320; (ii) generating a carrier gas stream for introduction into and through the chamber 322 including the iodine source 320, such that an iodine-laden gas exits the chamber 322 and into a conduit 330 for delivery to a nozzle 340; and (iii) ejecting the iodine-laden gas via the nozzle 340 onto the surface of the object, where it interacts with microbes contained on the surface of the object. Additionally, in some implementations, and as described above, the method may include intermediate steps of heating the iodine-laden gas and/or electrically charging the iodine-laden gas.

One of ordinary skill in the art will recognize that additional embodiments and implementations are also possible without departing from the teachings of the present invention. This detailed description, and particularly the specific details of the exemplary embodiments and implementations disclosed therein, is given primarily for clarity of understanding, and no unnecessary limitations are to be understood therefrom, for modifications will become obvious to those skilled in the art upon reading this disclosure and may be made without departing from the spirit or scope of the present invention.

What is claimed is:

1. A system for disinfecting a surface of an object, comprising:
    a carrier gas generation means, which generates a carrier gas;

a negative ion generator, which receives the carrier gas and ionizes molecules of the carrier gas;

a chamber including an iodine source, which receives the carrier gas after it has exited the negative ion generator, such that the carrier gas interacts with the iodine source and an iodine-laden gas exits the chamber; and an enclosure having an open side which is placed over or engages the surface of the object, the enclosure receiving the iodine-laden gas from the chamber, such that the iodine-laden gas interacts with microbes contained on the surface of the object.

2. The system as recited in claim 1, and further comprising:

a heater, which raises the temperature of the carrier gas.

3. The system as recited in claim 1, wherein the carrier gas is selected from the group consisting of air, carbon dioxide ($CO_2$), oxygen ($O_2$), nitrogen ($N_2$), and argon (Ar).

4. The system as recited in claim 1, wherein the iodine source is an iodine resin.

5. The system as recited in claim 1, and further comprising one or more carbon filters installed around a periphery of the open side of the enclosure.

6. The system as recited in claim 1, and further comprising a source of cleaning solution that is in fluid communication with the enclosure, such that the cleaning solution can be selectively introduced into the enclosure.

7. A method for disinfecting a surface of an object, comprising the steps of:

providing a chamber including an iodine source;

generating a carrier gas stream;

passing the carrier gas stream though a negative ion generator, which ionizes molecules of the carrier gas stream;

introducing the carrier gas stream into and through the chamber including the iodine source, such that an iodine-laden gas exits the chamber;

providing an enclosure having an open side, and placing the enclosure over or on the surface of the object; and introducing the iodine-laden gas into the enclosure, where it interacts with microbes contained on the surface of the object.

8. A system for disinfecting a surface of an object, comprising:

a carrier gas generation means, which generates a carrier gas;

a negative ion generator, which receives the carrier gas and ionizes molecules of the carrier gas;

a chamber including an iodine source, which receives the carrier gas after it has exited the negative ion generator, such that the carrier gas interacts with the iodine source and an iodine-laden gas exits the chamber; and a nozzle in fluid communication with the chamber for receiving the iodine-laden gas from the chamber, which is thus ejected from the nozzle and is applied to the surface of the object.

9. The system as recited in claim 8, and further comprising:

a heater, which raises the temperature of the carrier gas.

10. The system as recited in claim 8, wherein the carrier gas is selected from the group consisting of air, carbon dioxide ($CO_2$), oxygen ($O_2$), nitrogen ($N_2$), and argon (Ar).

11. The system as recited in claim 8, wherein the iodine source is an iodine resin.

12. A method for disinfecting a surface of an object, comprising the steps of:

providing a chamber including an iodine source;

generating a carrier gas stream;

passing the carrier gas stream though a negative ion generator, which ionizes molecules of the carrier gas stream;

introducing the carrier gas stream into and through the chamber including the iodine source, such that an iodine-laden gas exits the chamber and into a conduit for delivery to a nozzle; and ejecting the iodine-laden gas via the nozzle onto the surface of the object, where it interacts with microbes contained on the surface of the object.

\* \* \* \* \*